United States Patent [19]

Finger

[11] Patent Number: Plant 5,899

[45] Date of Patent: Mar. 10, 1987

[54] KALANCHOE PLANT NAMED INSPIRATION

[75] Inventor: Hermann Finger, Wiesmoor, Fed. Rep. of Germany

[73] Assignee: Wiesmoor-Gartnerie und Baumschule GmbH, Fed. Rep. of Germany

[21] Appl. No.: 750,602

[22] Filed: Jul. 1, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A new and distinct Kalanchoe plant named Inspiration, having abundant bright red flowers, semi-compact growth habit with excellent branching, dark green dense foliage, and good keeping qualities.

1 Drawing Figure

1

The present invention relates to a new and distinctive cultivar of Kalanchoe plant, botanically known as *Kalanchoe blossfeldiana,* and referred to by the cultivar name Inspiration.

Inspiration was developed by me through controlled breeding by crossing Singapur (seed parent) with Asmara (pollen parent). Singapur is disclosed in U.S. Plant Pat. No. 5,361.

Asexual reproduction of stem cuttings has shown that the unique features of this new Kalanchoe are stabilized and are reproduced true to type in successive propagations.

The following characteristics distinguish the new Kalanchoe from both its parent cultivars and other cultivated Kalanchoes of this type known and used in the floriculture industry:

1. Inspiration is characterized by its highly floriferous habit and excellent basal and side branching for a semi-compact plant.

2. Branching is similar to Singapur, Pollux (disclosed in U.S. Plant Pat. No. 4,816), and Attraction. The cultivar Attraction is disclosed in my pending application.

3. Inspiration is similar in height to Singapur and taller than Pollux and Attraction.

4. Foliage is dentate like Pollux and Attraction, but the leaves are more rounded like Singapur.

5. Leaf size, basal and self-branching, and highly floriferous nature make Inspiration suitable for 10 cm pot production.

6. After flower initiation plants must be treated with Alar in all seasons to reduce penduncle elongation.

7. Flowering time is 10 weeks in summer and 13 weeks in winter after start of short days, making Inspiration earlier than Pollux (11 weeks in summer) but not as early as Attraction and Singapur, both 9 week cultivars in summer.

8. Flower is a bright red, deeper in color than Attraction and similar to Pollux.

9. Flower size is similar to Singapur but not as large as Attraction or Pollux.

10. Flower petal shape is rounded like Singapur, rather than pointed like Pollux. Inspiration is highly floriferous as in Attraction and Singapur.

The accompanying colored photograph illustrates the overall appearance of this cultivar taken as a perspective view of the plant and showing the colors as true as it is reasonably possible to obtain in a colored reproduction of this type.

2

The following is a detailed description of my new Kalanchoe cultivar based on plants produced under commercial practices in the Greenhouses of Wiesmoor Gartnerei in Wiesmoor, Germany. Color references are made to The Royal Horticultural Society Colour Chart except where general terms of ordinary dictionary significance are used.

Parentage: A controlled cross between Singapur and Asmara.

Propagation:

(A) *Type cutting.*—Short stem cutting up to 2 cm long.

(B) *Time to root.*—10 days at 21° C. summer. 14 days at 21° winter.

(C) *Rooting habit.*—Many fine fibrous roots.

Plant description:

(A) *Form.*—Semi-compact, upright, best suited for growing and scheduling practices in 10 cm pots.

(B) *Habit of growth.*—Moderate rate of growth with good basal branching and branching every node.

(C) *Foliage description.*—Leaves simple, opposite, dark green in color. (1) Size: Mature leaf on a plant grown in a 10 cm pot is 110 mm long and 60 mm. wide. (2) Shape: Ovate with obtuse apex and acute base. (3) Texture: Glabrous, coriaceous, succulent. (4) Margin: Crenate. (5) Color: Young foliage, top side 137B; under side 137D; Mature foliage, top side 147A; under side 147B.

Flowering description:

(A) *Flowering habits.*—Cyme inflorescence; each shoot is formed by dichotomous branching, starting with the opening of the terminal flower of the main axis, followed by terminal flowers of the side branching, continuing with subsequent development of branches in the inflorescence. Major inflorescence is 50 mm to 60 mm in diameter and lateral inflorescences are 40 mm to 50 mm in diameter.

(B) *Natural flowering season.*—Early to mid January. Flowering time under controlled day length at 20° C. in summer is 10 weeks; in winter is 13 weeks. Flowering depends on temperature, light intensity, and other growing conditions.

(C) *Flower buds.*—Oblong, up to 10 mm long, developing to tubular as flower petals mature, sheathed with four light green sepals; corolla at maturity is 10 mm long.

(D) *Flowers borne.*—On compound dichasial cymes; peduncle is 3 mm to 4 mm in diameter, with peduncle length depending on growing conditions and Alar application; pedicels up to 8 mm long.

(E) *Quantity of flowers.*—Highly floriferous, main axis has over 125 flowers and lateral branches have over 75 flowers, with ten or more side branches in a 10 cm pot; excellent keeping qualities.

(F) *Petals.*—(1) Shape: Nearly round, top cuspidate. (2) Color: Top when opening, 44B, fading to 44C; under side, dark area 46D and light area 41D. (3) Number and size of petals: Four, united in corolla; petals 6 mm in diameter; flower 16 mm in diameter.

(G) *Reproductive organs.*—(1) Stamens: Eight in number. (a) Anther shape; Flat, elliptical; yellow in color. (b) Filament color: Light green. (c) Pollen color: Yellow. (2) Pistels: (a) Stigma: Flat shape, greenish white immature to white mature. (b) Style color: Light green. (c) Ovaries: Four-celled, 6 mm, green in color.

Disease resistance: Resistant to mildew. No other disease problems to date.

I claim:

1. A new and distinct cultivar of Kalanchoe named Inspiration, as described and illustrated, and particularly characterized by its abundant bright red flowers, semi-compact growth habit with excellent branching, dark green dense foliage, and its good keeping qualities.

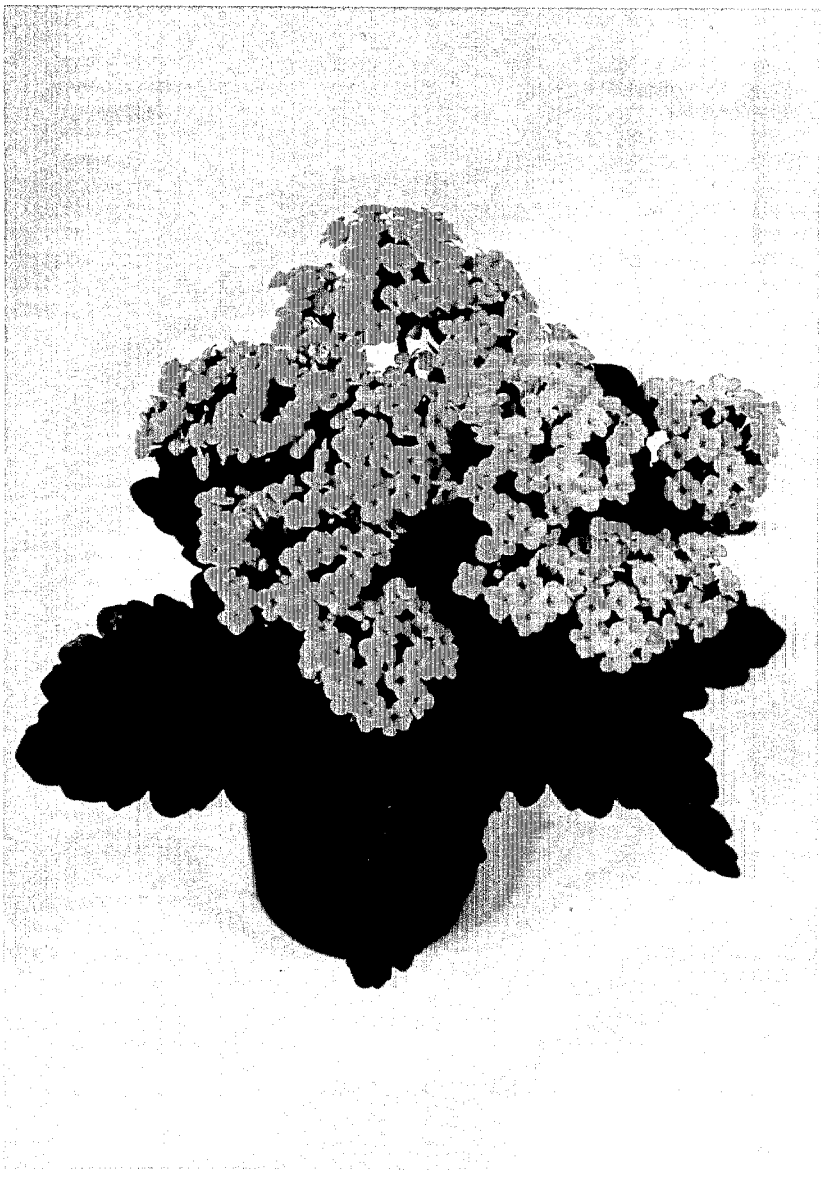

* * * * *